US008672926B2

(12) United States Patent
Van Hal et al.

(10) Patent No.: US 8,672,926 B2
(45) Date of Patent: *Mar. 18, 2014

(54) DEVICE FOR SHORTENING HAIRS BY MEANS OF LASER INDUCED OPTICAL BREAKDOWN EFFECTS

(75) Inventors: Robbert Adrianus Maria Van Hal, St-Oedenrode (NL); Reiko Verhagen, Vught (NL)

(73) Assignee: Koninklijke Philips N.V., Eindhoven (NL)

( * ) Notice: Subject to any disclaimer, the term of this patent is extended or adjusted under 35 U.S.C. 154(b) by 699 days.

This patent is subject to a terminal disclaimer.

(21) Appl. No.: 12/490,599

(22) Filed: Jun. 24, 2009

(65) Prior Publication Data

US 2009/0264872 A1 Oct. 22, 2009

Related U.S. Application Data

(63) Continuation of application No. 10/567,040, filed as application No. PCT/IB2004/051312 on Jul. 28, 2004, now Pat. No. 7,582,082.

(30) Foreign Application Priority Data

Aug. 4, 2003 (EP) .................................. 03102422

(51) Int. Cl.
*A61B 18/20* (2006.01)
(52) U.S. Cl.
USPC .................................. 606/9; 606/10; 128/898
(58) Field of Classification Search
USPC ............ 606/8–13, 16–18, 20–26; 607/88–96; 604/19, 20, 22; 128/898
See application file for complete search history.

(56) References Cited

U.S. PATENT DOCUMENTS 5,182,857 A 2/1993 Simon
5,653,706 A * 8/1997 Zavislan et al. ................... 606/9
(Continued)

FOREIGN PATENT DOCUMENTS

EP 0714739 A2 6/1996
EP 0754103 B1 11/1997
(Continued)

OTHER PUBLICATIONS

Christine Dierickx; "Laser-Assisted Hair Removal", Nov. 7, 2001, pp. 1-12. www.emedicine.com/derm/topic/562.htm.

(Continued)

*Primary Examiner* — Ahmed Farah

(57) ABSTRACT

The invention relates to a device for shortening hairs growing from human skin. The device has a laser source for generating a laser beam during a predetermined pulse time, an optical system for focusing the laser beam into a focal spot, and a laser beam manipulator for positioning the focal spot in a target position. According to the invention, a dimension of the focal spot and a power of the generated laser beam are such that, in the focal spot, the laser beam has a power density which is above a characteristic threshold value for hair tissue above which a laser induced optical breakdown (LIOB) phenomenon occurs in the hair tissue. The LIOB phenomenon results in a number of mechanical effects in the hair tissue, such as cavitation and the generation of shock waves, which damage the hair in positions surrounding the position in which the LIOB phenomenon occurs.

19 Claims, 2 Drawing Sheets

(56) References Cited

U.S. PATENT DOCUMENTS

Figure 1:
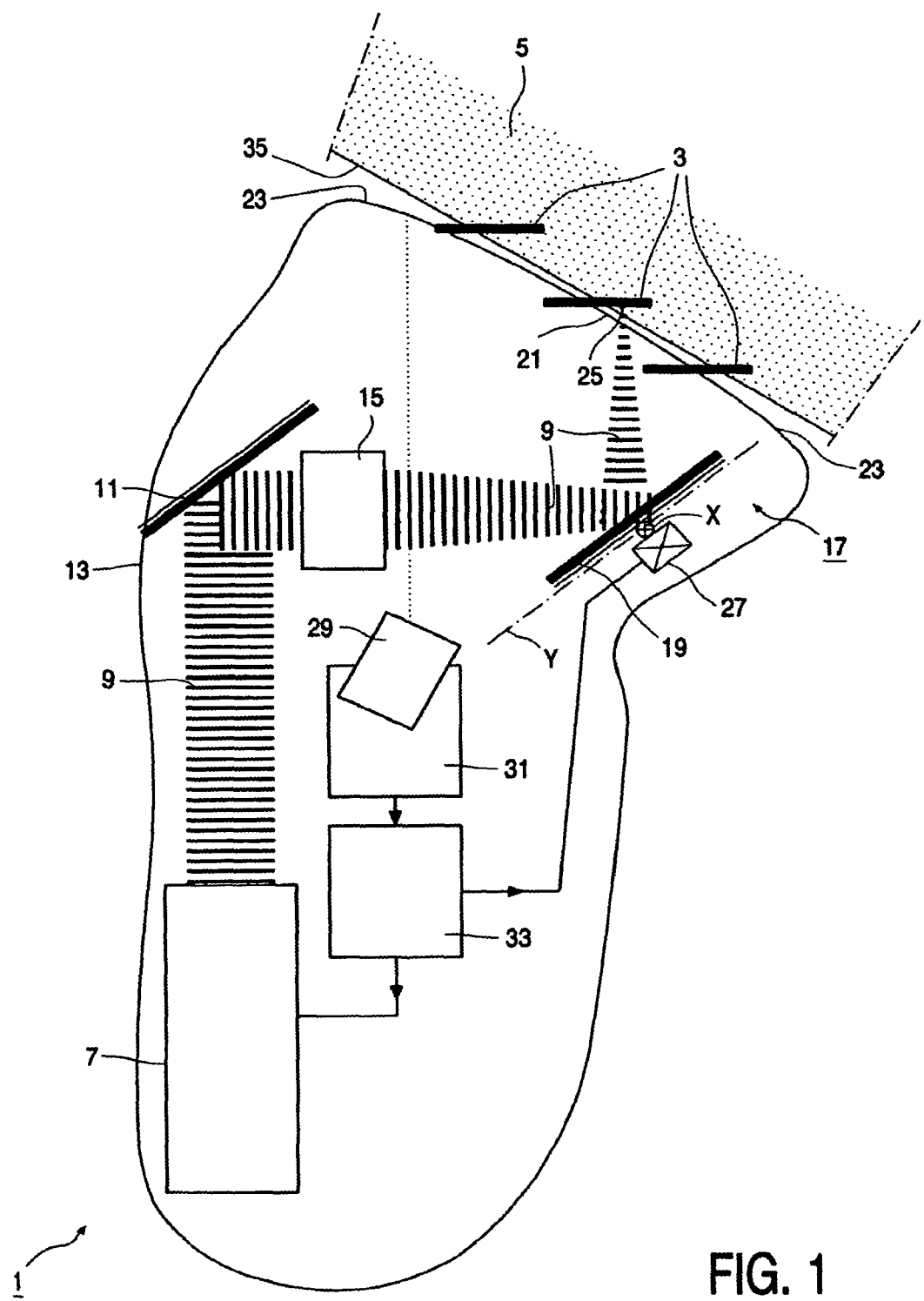

| | | | |
|---|---|---|---|
| 6,050,990 A * | 4/2000 | Tankovich et al. | 606/9 |
| 6,086,580 A | 7/2000 | Mordon et al. | |
| 6,267,771 B1 | 7/2001 | Tankovich et al. | |
| 6,517,888 B1 | 2/2003 | Weber | |
| 6,976,984 B2 * | 12/2005 | Cense et al. | 606/9 |
| 7,108,690 B1 * | 9/2006 | Lefki et al. | 606/10 |
| 7,582,082 B2 * | 9/2009 | Van Hal et al. | 606/10 |
| 2002/0195433 A1 | 12/2002 | Troitski | |

FOREIGN PATENT DOCUMENTS

| | | | |
|---|---|---|---|
| EP | 0913127 A2 | 5/1999 | |
| FR | 2590791 A1 | 6/1987 | |
| WO | 9308715 | 5/1993 | |
| WO | 9503089 | 2/1995 | |
| WO | 9533518 | 12/1995 | |
| WO | 9735526 A1 | 10/1997 | |
| WO | 9824507 A2 | 6/1998 | |
| WO | 0062700 A | 10/2000 | |

OTHER PUBLICATIONS

"More About Laser Hair Removal", www.shorelaser.com/LaserHairDet.htm.

Vogel et al: "Mechanisms of Intraocular Photodisruption With Picosecond and Nanosecond Laser Pulses"; Lasers in Surgery and Medicine, vol. 15, pp. 32-43, 1994.

* cited by examiner

DEVICE FOR SHORTENING HAIRS BY MEANS OF LASER INDUCED OPTICAL BREAKDOWN EFFECTS

The invention relates to a device for shortening hairs comprising a laser source for generating a laser beam during a predetermined pulse time, an optical system for focusing the laser beam into a focal spot, and a laser beam manipulator for positioning the focal spot in a target position.

A device for shortening hairs of the kind mentioned in the opening paragraph is known from WO-A-00/62700. The known device is a laser shaver which is suitable for use by non-professional persons, i.e. which is suitable for the consumer market, as a result of the fact that the device comprises a system which automatically positions the focal spot of the laser beam in a target position which corresponds to a position on a hair near the skin surface where the hair has to be melted, evaporated or burnt through. The laser beam of the known device has a wavelength for which the hair tissue has relatively high linear absorption properties. Preferably, a dimension of the focal spot of the laser beam corresponds to a diameter of the hairs, so that a hair present in the focal spot is locally heated in a uniform manner through its entire diameter. A sufficient amount of laser energy is concentrated in the focal spot, so that the portion of the hair present in the focal spot will melt, evaporate or burn and the hair is shortened.

A disadvantage of the known device for shortening hairs is that the total amount of energy, which is necessary to melt, evaporate or burn a hair through its entire diameter, is relatively high. Typically an amount of energy of 4 to 5 mJ is required to thermally break or cut a hair by means of the known device. In most cases said amount of energy is too high to avoid irritation or damage of the skin tissue surrounding the hair.

It is an object of the present invention to provide a device for shortening hairs of the kind mentioned in the opening paragraph by means of which hairs can be shortened by means of a significantly reduced amount of laser energy, so that irritation and damage of the skin tissue surrounding the hair are prevented as much as possible.

In order to achieve said object, a device for shortening hairs in accordance with the invention is characterized in that a dimension of the focal spot and a power of the generated laser beam are such that, in the focal spot, the laser beam has a power density which is above a characteristic threshold value for hair tissue above which, for the predetermined pulse time, a laser induced optical breakdown phenomenon occurs in the hair tissue.

In general, laser induced optical breakdown (LIOB) occurs in media, which are transparent or semi-transparent for the wavelength of a pulsed laser beam, when the power density of the laser beam in the focal spot exceeds a threshold value which is characteristic for the particular medium. Below the threshold value, the particular medium has relatively low linear absorption properties for the particular wavelength of the laser beam. Above the threshold value, the medium has strongly non-linear absorption properties for the particular wavelength of the laser beam, which are the result of ionization of the medium and the formation of plasma. This LIOB phenomenon results in a number of mechanical effects, such as cavitation and the generation of shock waves, which damage the medium in positions surrounding the position of the LIOB phenomenon.

From experiments it appeared that the LIOB phenomenon can be used to break and shorten hairs growing from skin. Hair tissue is transparent or semi-transparent for wavelengths between approximately 500 nm and 2000 nm. For each value of the wavelength within this range, LIOB phenomena occur in the hair tissue at the location of the focal spot when the power density of the laser beam in the focal spot exceeds a threshold value which is characteristic for the hair tissue. Said threshold value is rather close to the threshold value which is characteristic for aqueous media and tissue and is dependent on the pulse time of the laser beam. In particular, the threshold value of the required power density ($W/cm^2$) decreases when the pulse time increases. It appeared that, in order to achieve mechanical effects as a result of the LIOB phenomenon which are sufficiently effective so as to cause significant damage, i.e. at least initial breakage of a hair, a pulse time in the order of, for example, 10 ns suffices. For this value of the pulse time, the threshold value of the power density of the laser beam in the focal spot is in the order of $2*10^{10}$ $W/cm^2$. For the described pulse time and with a sufficiently small focal spot size obtained, for example, by means of a lens having a sufficiently large numerical aperture, this threshold value can be achieved with a total pulse energy of only a few tenths of a mJ. This total amount of pulse energy is significantly smaller than the total amount of pulse energy required to cause thermal breakage of the hair by means of the device known from WO-A-00/62700, and it appeared that for such values of the total pulse energy irritation and damage of the skin tissue surrounding the hair are limited to an acceptable level or even substantially completely prevented. An additional advantage of the invention is the occurrence of the so-called plasma shielding effect in the focal spot, which means that, as a result of the LIOB phenomenon, substantially all energy of the laser beam is absorbed in the focal spot. As a result, the device according to the invention has a relatively high efficiency, and irritation and damage of the skin tissue in positions behind the focal spot are prevented.

A particular embodiment of a device for shortening hairs in accordance with the invention is characterized in that a wavelength of the laser beam is between 800 nm and 1300 nm. For wavelengths within this range, both hair tissue and skin tissue surrounding the hairs are semi-transparent. As a result, the focal spot of the laser beam can be positioned in a position in or on the hair below the skin surface, so that the device provides an optimum smoothness of the skin which is maintained for a relatively long time. Since the skin tissue and the hair tissue are semi-transparent for the wavelength of the laser beam and the LIOB phenomenon only occurs in the focal spot of the laser beam, only a relatively small portion of the energy of the laser beam is absorbed or scattered by the skin tissue and the hair tissue which are present in the laser beam between the laser source and the focal spot. As a result, hardly any irritation of said skin tissue and damage of said hair tissue occur, and a relatively large portion of the energy of the generated laser beam is used to effect the LIOB phenomenon in the focal spot.

A further embodiment of a device for shortening hairs in accordance with the invention is characterized in that the wavelength is between 1000 nm and 1100 nm. For wavelengths within this range, the linear absorption properties of the hair tissue are at a minimum, so that a maximum portion of the energy of the generated laser beam is used to generate the LIOB phenomenon in the focal spot of the laser beam.

A particular embodiment of a device for shortening hairs in accordance with the invention is characterized in that the device comprises an image sensor for detecting an image of at least a portion of a skin with hairs to be shortened, an image recognizing system for determining a position and/or orientation of the hairs relative to the skin, and a control system for determining the target position of the focal spot as a function of said position and/or orientation, wherein, during operation, the control system adjusts the laser beam manipulator into a position corresponding to the target position of the focal spot and, subsequently, activates the laser source. In this particular embodiment, the target position of the focal spot of the laser beam is automatically determined by the control system, and the control system automatically activates the laser source when having adjusted the laser beam manipulator into a position corresponding to the target position. As a result of this automatic determination and positioning of the focal spot, the device for shortening hairs is particularly suitable for use by non-professional persons, i.e. is particularly suitable for the consumer market.

A further embodiment of a device for shortening hairs in accordance with the invention is characterized in that, during operation, for each target position the control system activates the laser source so as to generate a plurality of laser pulses with the predetermined pulse time. Since in this further embodiment the laser source generates a plurality of laser pulses for each target position, the required energy per pulse is significantly reduced, so that the required energy capacity of the laser source is significantly reduced.

A further embodiment of a device for shortening hairs in accordance with the invention is characterized in that, during operation, the control system consecutively adjusts the laser beam manipulator into a number of adjacent target positions on an imaginary line extending through a hair to be shortened transversely to a longitudinal direction of the hair. In this further embodiment, an LIOB phenomenon is consecutively effected in each target position on said imaginary line, and each LIOB phenomenon causes a local damage or initial breakage of the hair, so that the total damage caused by the consecutively effected LIOB phenomena causes total breakage of the hair along said imaginary line.

Figure 2:
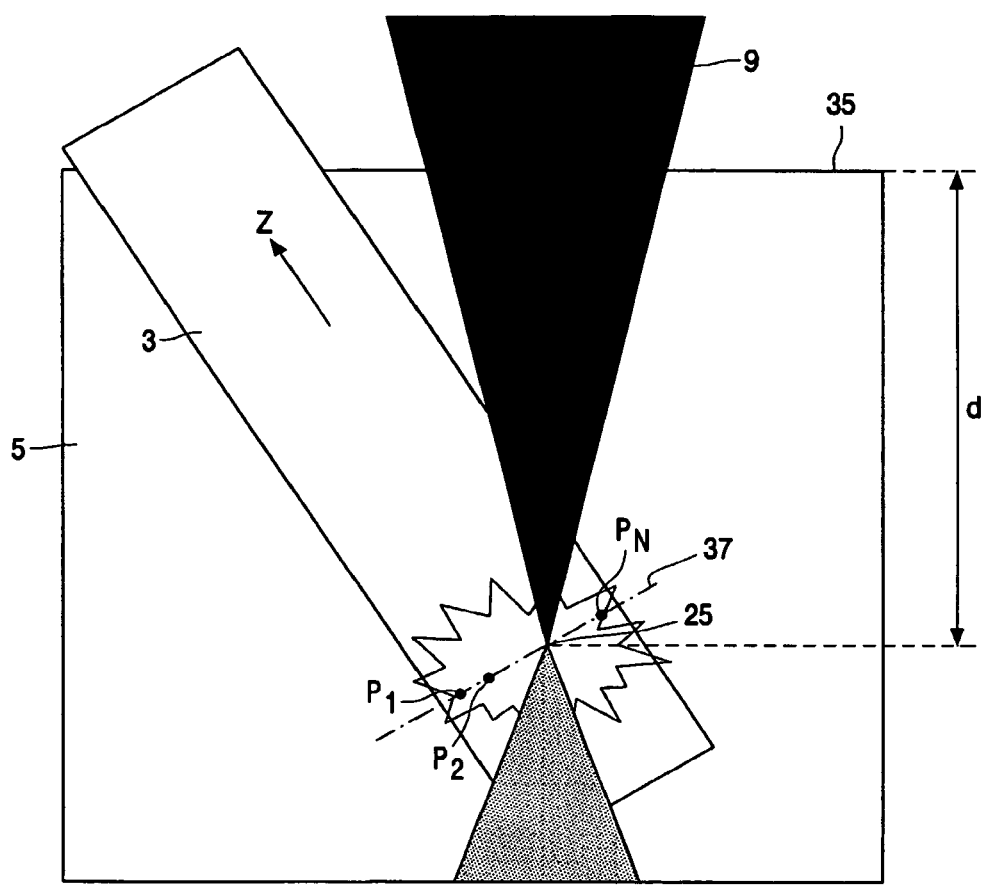

In the following, embodiments of a device for shortening hairs in accordance with the invention will be explained in further detail with reference to the figures, wherein:

FIG. 1 schematically shows a device for shortening hairs in accordance with the invention, and FIG. 2 shows in detail a target position of a focal spot of a laser beam of the device of FIG. 1 on a hair to be shortened.

In FIG. 1, only the main components of a device 1 for shortening hairs 3 growing from human skin 5 are schematically shown. The device 1 comprises a laser source 7 for generating a laser beam 9 during a predetermined pulse time. In the embodiment shown, the laser source 7 is a pulsed Nd:YAG laser and the generated laser beam 9 has a wavelength of 1064 nm. The generated laser beam 9 follows an optical path from the laser source 7 towards the skin 5 via a first mirror 11, which is mounted in a fixed position in a housing 13 of the device 1, an optical system 15 comprising a lens system or objective, a laser beam manipulator 17 comprising a second mirror 19, and a radiation exit window 21, which is provided in a skin contact surface 23 of the housing 13. The optical system 15 focuses the laser beam 9 into a focal spot 25. The laser beam manipulator 17 comprises an electrical driving member 27 which is only schematically shown in FIG. 1 and by means of which the second mirror 19 is pivotable about a first pivot axis X, which extends parallel to a surface of the second mirror 19 and parallel to the skin contact surface 23, and about a second pivot axis Y, which extends parallel to the surface of the second mirror 19 and perpendicularly to the first pivot axis X. By means of pivotal motions of the second mirror 19 about the first and the second pivot axes X and Y, the focal spot 25 is positioned by the laser beam manipulator 17 in a target position which is determined in a manner described in the following.

As schematically shown in FIG. 1, the device 1 further comprises an image sensor 29 which is mounted in a fixed position in the housing 13 for detecting an image of at least a portion of the skin 5 with the hairs 3 to be shortened. In the embodiment shown, the image sensor 29 is a CCD camera. The device 1 further comprises an image recognizing system 31 for determining a position and/or orientation of the hairs 3 relative to the skin 5 on the basis of an image of the skin 5 generated by the image sensor 29. The target position of the focal spot 25 is determined by a control system 33 of the device 1 on the basis of the position and/or orientation of the hairs 3 relative to the skin 5 as determined by the image recognizing system 31. A detailed description of the operation of the image recognizing system 31 and the control system 33 is omitted here for the sake of simplicity. However, reference is made to WO-A-00/62700. The hair-removing device described therein has a similar image recognizing system and control system, and the operation thereof is described in detail therein. On the basis of said description in WO-A-00/62700, the person skilled in the art will be able to design and adapt the image recognizing system 31 and the control system 33 so as to be suitable for their purposes in the device 1. When the target position has been determined, the control system 33 adjusts the driving member 27 of the laser beam manipulator 17 and, consequently, the second mirror 19 into a position which corresponds to the target position. Subsequently, the control system 33 activates the laser source 7. As in this manner the target position of the focal spot 25 of the laser beam 9 is automatically determined by the control system 33, and the control system 33 automatically activates the laser source 7 when having adjusted the position of the laser beam manipulator 17, the device 1 is particularly suitable for use by non-professional persons, i.e. is particularly suitable for the consumer market.

As schematically shown in FIG. 2, in the embodiment shown the control system 33 determines the target position of the focal spot 25 of the laser beam 9 in such a manner, that the focal spot 25 is present in a portion of the hair 3 which is present at a distance d below the skin surface 35. In the embodiment shown, said distance d is approximately 0.1 mm. According to the invention, a dimension of the focal spot 25 and a power of the laser beam 9 generated by the laser source 7 are such that, in the focal spot 25, the laser beam 9 has a power density which is above a characteristic threshold value for hair tissue above which, for the predetermined pulse time of the laser beam 9, a laser induced optical breakdown (LIOB) phenomenon occurs in the hair tissue at the location of the focal spot 25. Said LIOB phenomenon is used to mechanically break the hair 3 as will be further described in the following.

In general, the LIOB phenomenon occurs in a medium, which is transparent or semi-transparent for the wavelength of a laser beam, when the power density of the laser beam exceeds a threshold value which is characteristic for the particular medium. Below the threshold value, the medium has a relatively small linear absorption coefficient for the particular wavelength of the laser beam. Above the threshold value, the medium has a strongly non-linear absorption coefficient for the particular wavelength of the laser beam, which is the result of ionization of the medium and the formation of plasma. The LIOB phenomenon results in a number of mechanical effects, such as cavitation and the generation of shock waves, which damage the medium in positions surrounding the position of the LIOB phenomenon.

Since the laser beam 9 is focused into the focal spot 25, the power density of the laser beam 9 will have a maximum value in the focal spot 25. As a result, when the power of the laser beam 9 is gradually increased, an LIOB phenomenon will first occur in the focal spot 25. The dimension of the focal spot 25 and the power of the laser beam 9 are such that the LIOB phenomenon substantially only occurs in the focal spot 25. In the embodiment of the device 1 according to the invention, the wavelength of the laser source 7 (1064 nm) is a wavelength for which both the hair tissue and the skin tissue present between the skin surface 35 and the focal spot 25 are semi-transparent. As a result, absorption and scattering of the laser beam 9 by the hair tissue and the skin tissue present between the skin surface 35 and the focal spot 25 will be relatively small, so that a relatively large portion of the energy of the generated laser beam 9 is used to effect the LIOB phenomenon in the focal spot 25 and hardly any irritation of the skin tissue and damage of the hair tissue present between the skin surface 35 and the focal spot 25 occur. It is noted that, in general, the skin tissue present immediately below the skin surface 35 is semi-transparent for wavelengths in the range between approximately 800 nm and 1300 nm. As a consequence, embodiments of a device for shortening hairs in positions below the skin surface 35 should preferably have a laser source with a wavelength within said range. Preferably, for shortening hairs below the skin surface 35 the wavelength is in the range between approximately 1000 nm and 1100 nm, as in the embodiment of FIG. 1, since for wavelengths within said range the linear absorption and scattering properties of the hair tissue and the skin tissue immediately below the skin surface 35 are at a minimum.

Experiments have shown that the above described mechanical effects, which result from the LIOB phenomenon in the focal spot 25 in the hair 3, can lead to breakage of the hair 3 or at least to initial breakage of the hair 3 in an area immediately surrounding the focal spot 25. In order to achieve an LIOB phenomenon in the focal spot 25, the power density of the laser beam 9 in the focal spot 25 should be above the characteristic threshold value for hair tissue as mentioned before. It is noted that said characteristic threshold value for hair tissue is rather close to the threshold value which is characteristic for the occurrence of LIOB phenomena in aqueous media and aqueous tissue. Furthermore, said characteristic threshold value is dependent on both the value of the wavelength and on the value of the pulse time of the laser source 7. In particular, the threshold value ($W/cm^2$) decreases when the pulse time increases. The skilled person will be able to determine said threshold value by means of experiments.

Experiments have further shown that, in order to achieve that the mechanical effects resulting from the LIOB phenomenon are sufficiently strong to cause significant damage of the hair tissue in the focal spot 25, i.e. to cause at least initial breakage of the hair 3 in the focal spot 25, a pulse time of the laser source 7 in the order of, for example, 10 ns suffices. In the embodiment of the device 1 shown in FIG. 1, the Nd:YAG laser source 7 has a pulse time of 8 ns. For a value of the pulse time in the order of 10 ns, the threshold value of the power density of the laser beam 9 in the focal spot 25 is in the order of $2*10^{10}$ $W/cm^2$. Although this threshold value is enormous, it can be readily achieved for the described pulse time with a sufficiently small size of the focal spot 25 and with a total pulse energy of no more than a few tenths of a mJ. The required size of the focal spot 25 is in the order of 10 µm, which is substantially smaller than the average diameter of a hair (100 µm) and can be realized by means of a sufficiently large numerical aperture of the lens system or objective of the optical system 15. In view of said small amount of total pulse energy, irritation and damage of the skin tissue surrounding the hair 3 to be shortened are limited to an acceptable level or even substantially completely prevented. Another advantage of the device 1 in accordance with the invention is that the device 1 provides an optimum smoothness of the skin 5 which is maintained for a relatively long time, in view of the fact that the hairs 3 are broken below the skin surface 35.

The invention also encloses embodiments in which the position of the focal spot 25 of the laser beam 9 is on or above the skin surface 35, so that the hairs 3 are shortened to a length just on or above the level of the skin surface 35. An advantage of such embodiments is that the wavelength of the laser beam 9 does not need to be in a range for which the skin tissue, which is present immediately below the skin surface 35, is transparent or semi-transparent. In such embodiments, the wavelength of the laser beam 9 should be in a range for which only the hair tissue is transparent or semi-transparent. This range is substantially wider than the range between 800 nm and 1300 nm mentioned before and lies between approximately 500 nm and 2000 nm. It is noted that, in embodiments in which the hairs are broken above the skin surface 35, better results are obtained if a hair supporting gel is applied on the skin 5 before treatment with the device 1.

From the foregoing description it is clear that local damage or initial breakage of the hair 3 in the focal spot 25 can be achieved with a single pulse of the laser beam 9 having a pulse time in the order of 10 ns and a total amount of pulse energy of no more than a few tenths of a mJ. However, in order to achieve complete breakage of the hair 3, a significantly higher total amount of energy is required. This can be achieved, for example, by means of a single pulse having a significantly higher amount of total pulse energy. This, however, requires a relatively high energy capacity of the laser source 7, as a result of which the dimensions and/or the costs of the laser source 7 may become unacceptably high for a product suitable for the consumer market. In the embodiment of the device 1 shown in FIG. 1, the total amount of energy required to completely break the hair 3 is provided in that, for each target position of the focal spot 25, the control system 33 activates the laser source 7 so as to generate a plurality of laser pulses with the predetermined pulse time of 8 ns and a pulse energy of 0.2 mJ. In the embodiment shown in FIG. 1, the laser source 7 has a pulse frequency of 100 Hz, and the laser source 7 is activated in each target position during a period of approximately 50 ms, so that in each target position the laser source 7 will generate approximately 5 such laser pulses. In addition, as shown in FIG. 2, for each hair 3 to be shortened the control system 33 consecutively adjusts the laser beam manipulator 17 into a number N of adjacent target positions $T_1, T_2, \ldots, T_N$ lying at regular intervals on an imaginary line 37, which extends through the hair 3 transversely to the longitudinal direction Z of the hair 3 at the location where the hair 3 is to be shortened. In this way, the energy per laser pulse required to achieve initial breakage of the hair 3 in each target position $T_1, T_2, T_N$ is limited, so that the required energy capacity of the laser source 7 is limited, and the initial damages consecutively achieved by the LIOB phenomena in all target positions $T_1, T_2, T_N$ lead to total breakage of the hair 3 along said imaginary line 37.

It is noted that local damage of the hairs 3 by means of an LIOB phenomenon in the focal spot 25 can also be achieved by means of laser pulses having a predetermined pulse time which is considerably smaller than the example of 8 ns in the embodiment described before. Provided that the laser pulses have a sufficient pulse energy, pulse times in the order of pico seconds ($10^{-12}$ s) or femto seconds ($10^{-15}$ s) are also effective to cause local damage of the hairs 3, and complete breakage of the hairs 3 can be achieved by a sufficient number of pulses in a sufficient number of different target positions in or on the hairs 3.

It is noted that, in the above description of the invention and in the claims, the required dimension of the focal spot 25 and the required power of the generated laser beam 9 are defined in terms of the result to be achieved, i.e. the dimension of the focal spot 25 and the power of the generated laser beam 9 should be such that, in the focal spot 25, the laser beam 9 has a power density (W/cm$^2$) which is above the characteristic threshold value above which LIOB phenomena occur in hair tissue. It is however noted that, for a given laser source with a predetermined pulse time and pulse energy, the skilled person will be able to determine the required dimension of the focal spot on the basis of the pulse time, the pulse energy, and the characteristic threshold value of the power density in the focal spot, and that the skilled person will also be able to design a suitable optical system which provides the necessary dimension of the focal spot. It will further be obvious for the skilled person that, if a laser source is used having a higher pulse energy, the total number of laser pulses required to completely break a hair will be reduced.

It is further noted that the invention also covers embodiments in which the device has another kind of optical system for focusing the laser beam into a focal spot. Instead of a lens system or objective, for example, a curved mirror may be used. The optical system may for example comprise a beam expander followed by the lens system or objective, which will result in a further reduction of the focal spot size. It is noted that the position of the focal spot 25 in a direction perpendicular to the exit window 21 and the skin surface 35 is determined by the optical properties of the optical system 15 and by the position of the optical system 15 in the optical path between the laser source 7 and the exit window 21. Said position of the focal spot 25 determines the length of the hairs 3 after being shortened. It is noted that a device in accordance with the invention may be additionally provided with an actuator for adjusting said position of the optical system 15 or with a device for adjusting the optical properties of the optical system 15, so that the position of the focal spot 25 in said direction perpendicular to the skin surface 35 may be manually or automatically adjusted. It is finally noted that the invention also covers embodiments in which the laser beam manipulator and/or the laser source are not automatically controlled by a control system 33, but are to be operated and controlled by a professional operator of the device.

The invention claimed is:

1. A device, comprising:
   a laser source generating a laser beam;
   an optical system focusing the laser beam into a focal spot;
   a laser beam manipulator positioning the focal spot in a target position;
   a control system determining the target position, adjusting the laser beam manipulator to position the focal spot in the target position, and activating the laser source after adjusting the laser beam manipulator;
   an image sensor detecting an image of a portion of skin including hairs; and
   an image recognizing system determining one of a position and an orientation of the hairs relative to the skin,
   wherein the control system determines the target position based on the one of the position and orientation of the hairs, and
   wherein the laser beam damages hair tissue via a mechanical effect, the mechanical effect including cavitation.

2. The device of claim 1, wherein the control system determines the target position to be a portion of the hairs that is below a surface of the skin.

3. The device of claim 2, wherein a wavelength of the laser beam is in a range of 800-1300 nanometers.

4. The device of claim 1, wherein the control system determines the target position to be a portion of the hairs that is above a surface of the skin.

5. The device of claim 4, wherein a wavelength of the laser beam is in a range of 500-2000 nanometers.

6. The device of claim 1, wherein the control system determines a plurality of target positions and activates the laser source to generate a plurality of laser pulses having a predetermined pulse time and predetermined pulse energy for each target position.

7. The device of claim 6, wherein the plurality of target positions correspond to a number of adjacent positions through a hair, wherein the laser pulses create a breakage of the hair at each target position and the breakages at all the target positions cause a total breakage of the hair.

8. The device of claim 6, wherein the predetermined pulse time is in the range of 8-10 nanoseconds.

9. The device of claim 6, wherein the predetermined pulse energy is substantially 0.2 milliJoules.

10. A device, comprising:
    a laser source generating a laser beam;
    an optical system focusing the laser beam into a focal spot; and
    a laser beam manipulator positioning the focal spot in a target position, the target position being located in hair tissue, wherein the focal spot has a power density above a threshold value for hair tissue causing a laser induced optical breakdown (LIOB) in the hair tissue, wherein the LIOB damages the hair tissue via a mechanical effect, the mechanical effect including cavitation.

11. The device of claim 10, wherein the optical system further comprises one of a lens system and an object lens.

12. The device of claim 10, wherein the laser beam manipulator further comprises a mirror and a radiation exit window.

13. The device of claim 12, wherein the radiation exit window is configured to be in contact with a portion of skin including the hair tissue.

14. The device of claim 12, wherein the laser beam manipulator further comprises a driving member to pivot the mirror about at least two axes.

15. The device of claim 10, wherein the power density is in the order of $2*10^{10}$ W/cm$^2$.

16. The device of claim 10, wherein a size of the focal spot is in the order of 10 micrometers.

17. A method, comprising:
    generating a laser beam;
    focusing the laser beam into a focal spot; and
    positioning the focal spot in a target position, the target position being located in hair tissue,
    wherein the focal spot has a power density above a threshold value for hair tissue causing a laser induced optical breakdown (LIOB) in the hair tissue, wherein the LIOB damages the hair tissue via a mechanical effect, the mechanical effect including cavitation.

18. The method of claim 17, further comprising: determining the target position; and activating the laser beam after the target position is determined.

19. The method of claim 17, further comprising: detecting an image of a portion of skin including hairs; and determining one of a position and an orientation of the hairs relative to the skin, wherein the target position is determined based on the one of the position and orientation of the hairs.

\* \* \* \* \*